US00PP26491P2

(12) United States Plant Patent
Heuger

(10) Patent No.: US PP26,491 P2
(45) Date of Patent: Mar. 8, 2016

(54) ***HELLEBORUS* PLANT NAMED 'COSEH 3060'**

(50) Latin Name: ***Helleborus niger*×*Helleborus sternii***
Varietal Denomination: COSEH 3060

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 184 days.

(21) Appl. No.: 13/999,081

(22) Filed: Jan. 10, 2014

(51) Int. Cl.
*A01H 5/02* (2006.01)

(52) U.S. Cl.
USPC ..... Plt./439

(58) Field of Classification Search
USPC ..... Plt./439
See application file for complete search history.

*Primary Examiner* — Anne Grunberg
(74) *Attorney, Agent, or Firm* — C. A. Whealy

(57) ABSTRACT

A new and distinct cultivar of *Helleborus* plant named 'COSEH 3060', characterized by its relatively compact, upright and mounding plant habit; uniform and freely flowering habit; dark green-colored leaves; freely and early flowering habit; single white and yellow green-colored flowers; and good garden performance.

2 Drawing Sheets

Botanical designation: *Helleborus niger*×*Helleborus sternii*.

Cultivar denomination: 'COSEH 3060'.

BACKGROUND OF THE INVENTION

The present invention relates to a new and distinct cultivar of *Helleborus* plant, botanically known as *Helleborus niger*× *Helleborus sternii* and hereinafter referred to by the name 'COSEH 3060'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and resistance to pests common to *Helleborus* plants.

The new *Helleborus* plant originated from a cross-pollination conducted by the Inventor in Glandorf, Germany in November, 2006 of an unnamed proprietary seedling selection of *Helleborus niger*, not patented, as the female, or seed, parent with an unnamed proprietary seedling selection of *Helleborus sternii*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2008.

Asexual reproduction of the new *Helleborus* plant by divisions in a controlled environment in Glandorf, Germany since February, 2009 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 3060'. These characteristics in combination distinguish 'COSEH 3060' as a new and distinct *Helleborus* plant:

1. Relatively compact, upright and mounding plant habit.
2. Uniform and freely flowering habit.
3. Dark green-colored leaves.
4. Freely and early flowering habit.
5. Single white and yellow green-colored flowers.
6. Good garden performance.

Compared to plants of the parent selections, plants of the new *Helleborus* are more uniformly mounded and are more freely flowering.

Plants of the new *Helleborus* can be compared to plants of *Helleborus niger*×*Helleborus lividus* 'COSEH 710', disclosed in U.S. Plant Pat. No. 21,063. In side-by-side comparisons conducted in Glandorf, Germany, plants of the new *Helleborus* differed primarily from plants of 'COSEH 710' in the following characteristics:

1. Plants of the new *Helleborus* were more compact than and not as vigorous as plants of plants of 'COSEH 710'.
2. Plants of the new *Helleborus* flowered earlier than plants of 'COSEH 710'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 3060' grown in a container.

The photograph on the second sheet is a close-up view of a typical flower and flower buds of 'COSEH 3060'.

DETAILED BOTANICAL DESCRIPTION

The aforementioned photographs and following observations, measurements and values describe plants grown during the autumn in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus sternii* 'COSEH 3060'.

Parentage:

*Female, or seed, parent*.—Unnamed proprietary seedling selection of *Helleborus niger*, not patented.

*Male, or pollen, parent*.—Unnamed proprietary seedling selection of *Helleborus sternii*, not patented.

Propagation:

*Type*.—By tissue culture.

*Time to initiate roots, winter*.—About two months at temperatures about 12° C.

*Time to produce a rooted young plant, winter*.—About six months at temperatures ranging from 4° C. to 15° C.

*Root description*.—Thick to thin, fleshy; white to brown in color.

*Rooting habit*.—Sparse.

Plant description:

*Plant and growth habit*.—Herbaceous perennial; relatively compact, upright and mounding plant habit with flowers held just above the foliar plane; plant shape is roughly globular; growth habit, low vigor.

*Plant height, soil level to top of foliar plane*.—About 10.3 cm.

*Plant height, soil level to top of flowers*.—About 13.5 cm.

*Plant diameter* (*area of spread*).—About 30.9 cm.

Leaf description:

*Arrangement*.—Leaves arranged in a basal rosette; leaves palmately compound with five leaflets per leaf.

*Leaf length*.—About 11.7 cm.

*Leaf width*.—About 13.9 cm.

*Leaflet length*.—About 7.4 cm.

*Leaflet width*.—About 3.1 cm.

*Leaf shape*.—Palmate; orbicular to reniform in outline.

*Leaflet shape*.—Narrowly ovate to narrowly elliptic; slightly curved.

*Leaflet apex*.—Acute to narrowly acute.

*Leaflet base*.—Attenuate.

*Leaflet margin*.—Serrate.

*Leaflet texture, upper and lower surfaces*.—Smooth, glabrous; leathery.

*Leaflet luster, upper surface*.—Moderately glossy.

*Leaflet luster, lower surface*.—Slightly glossy.

*Leaflet venation pattern*.—Pinnate.

*Leaflet color*.—Developing leaves, upper surface: Between 143A and 146A. Developing leaves, lower surface: Close to 148A. Fully developed leaves, upper surface: Darker than between N137A and 147A; venation, close to 144A. Fully developed leaves, lower surface: Between 147B and 148B; venation, close to N186C.

*Petioles*.—Length: About 8.6 cm. Diameter: About 5 mm. Texture, upper and lower surfaces: Smooth, glabrous. Color, upper and lower surfaces: Close to 145B heavily tinged and speckled with between 177A and 200C.

Flower description:

*Flower shape and habit*.—Single rotate flowers in terminal racemes; freely and uniform flowering habit with about 33 flowers per raceme; flowers facing upright to outwardly.

*Fragrance*.—None detected.

*Natural flowering season*.—Plants begin flowering about ten months after planting; plants flower from autumn into winter in Germany.

*Flower longevity on the plant*.—About ten days; flowers not persistent.

*Inflorescence height*.—About 10.7 cm.

*Inflorescence diameter*.—About 11.7 cm.

*Flower buds*.—Length: About 2.1 cm. Diameter: About 1.4 cm. Shape: Broadly obovate to broadly ovate. Color: Close to 150D strongly tinged and flushed with close to 174A to 174D; towards the apex, close to 157B to 157D; venation, close to 187D.

*Flower diameter*.—About 6.7 cm.

*Flower depth* (*height*).—About 2.6 cm.

*Petals*.—Transformed into nectaries.

*Sepals*.—Quantity and arrangement: Five, arranged in a single whorl. Length: About 3.3 cm. Width: About 2.7 cm. Shape: Ovate. Apex: Bluntly acute. Base: Broadly cuneate. Margin: Entire. Texture, upper and lower surfaces: Smooth, glabrous. Color: When opening, upper surface: Between 150D and 155A. When opening, lower surface: Between 150D and 155A moderately to heavily tinged and flushed with between 177D and 199D and 184B to 184C. Fully opened, upper surface: Close to 150D; towards the apex, close to 145B to 145C; towards the base, close to 144C. Fully opened, lower surface: Close to 150D slightly to moderately tinged and flushed with between 177D and 199D and 184B.

*Peduncles*.—Length: About 6 cm. Diameter: About 4.5 mm. Aspect: About 25° from vertical. Strength: Moderately strong. Texture: Smooth, glabrous. Color: Close to 173A to 173B; towards the base, tinged with close to 199C.

*Pedicels*.—Length: About 1.8 cm. Diameter: About 2 mm. Aspect: About 20° from peduncle axis. Strength: Moderately strong. Texture: Smooth, glabrous. Color: Close to 173A to 173B; towards the base, tinged with close to 199C.

*Reproductive organs*.—Stamens: Quantity per flower: About 80. Filament length: About 1.4 cm. Filament color: Close to NN155D. Anther shape: Reniform; basifixed. Anther length: About 2 mm. Anther color: Close to 150C. Pollen amount: Scarce. Pollen color: Close to 4D. Pistils: Quantity per flower: About five to seven. Pistil length: About 9 mm. Stigma shape: Club-shaped. Stigma color: Close to 157D. Style length: About 8.5 mm. Style color: Close to 155A. Ovary color: Close to 145B to 145C. Nectaries (transformed petals): Quantity per flower: About 13. Length: About 9 mm. Diameter: About 2 mm. Shape: Tubular, flattened. Color, immature, inner and outer surfaces: Close to 144A; towards the apex, close to 145B. Color, mature, inner and outer surfaces: Close to 144A to 144B; towards the apex, close to 154B.

*Seeds and fruits*.—Seed and fruit development have not been observed on plants of the new *Helleborus*.

Garden performance: Plants of the new *Helleborus* have been observed to have good garden performance and to tolerate rain, wind and high temperatures about 35° C. and to be hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 3060' as illustrated and described.

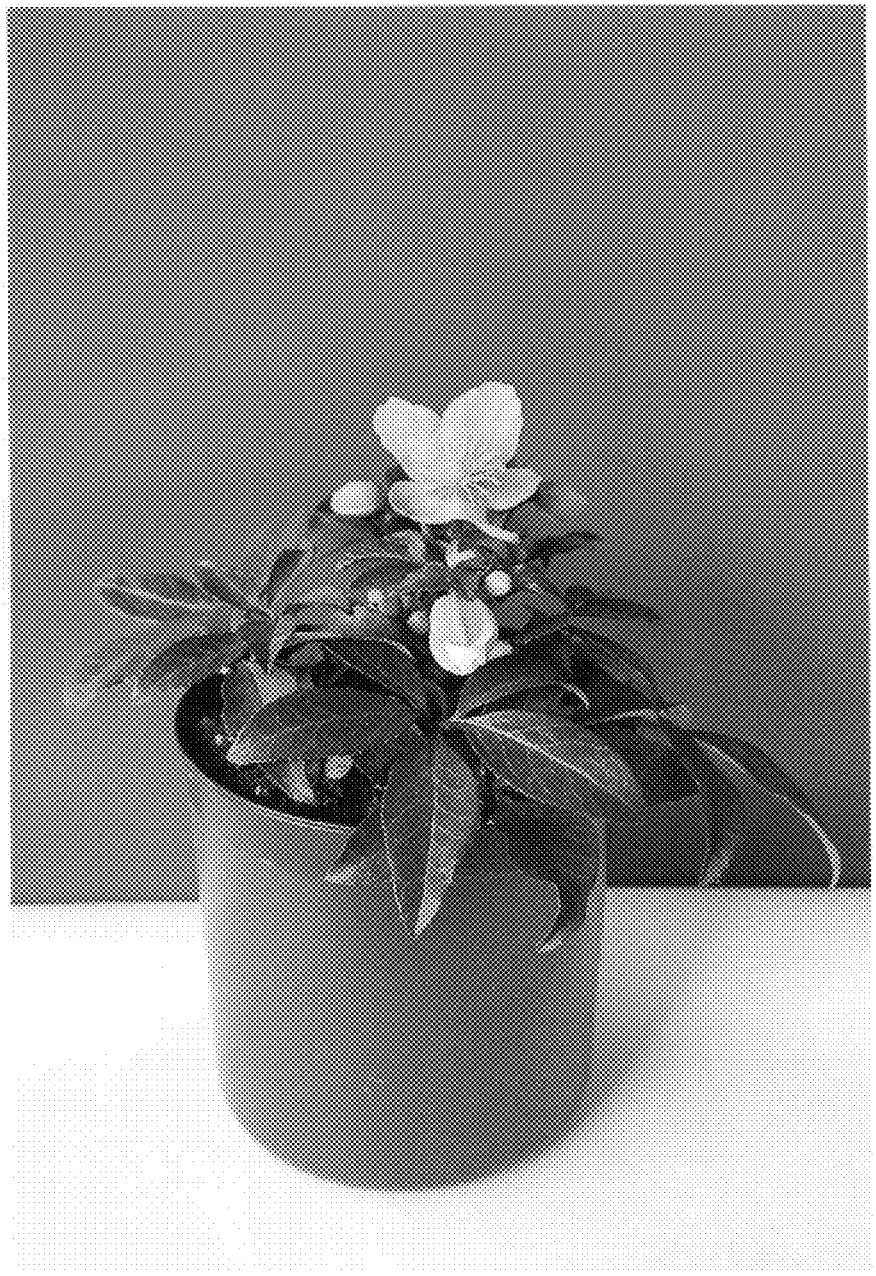

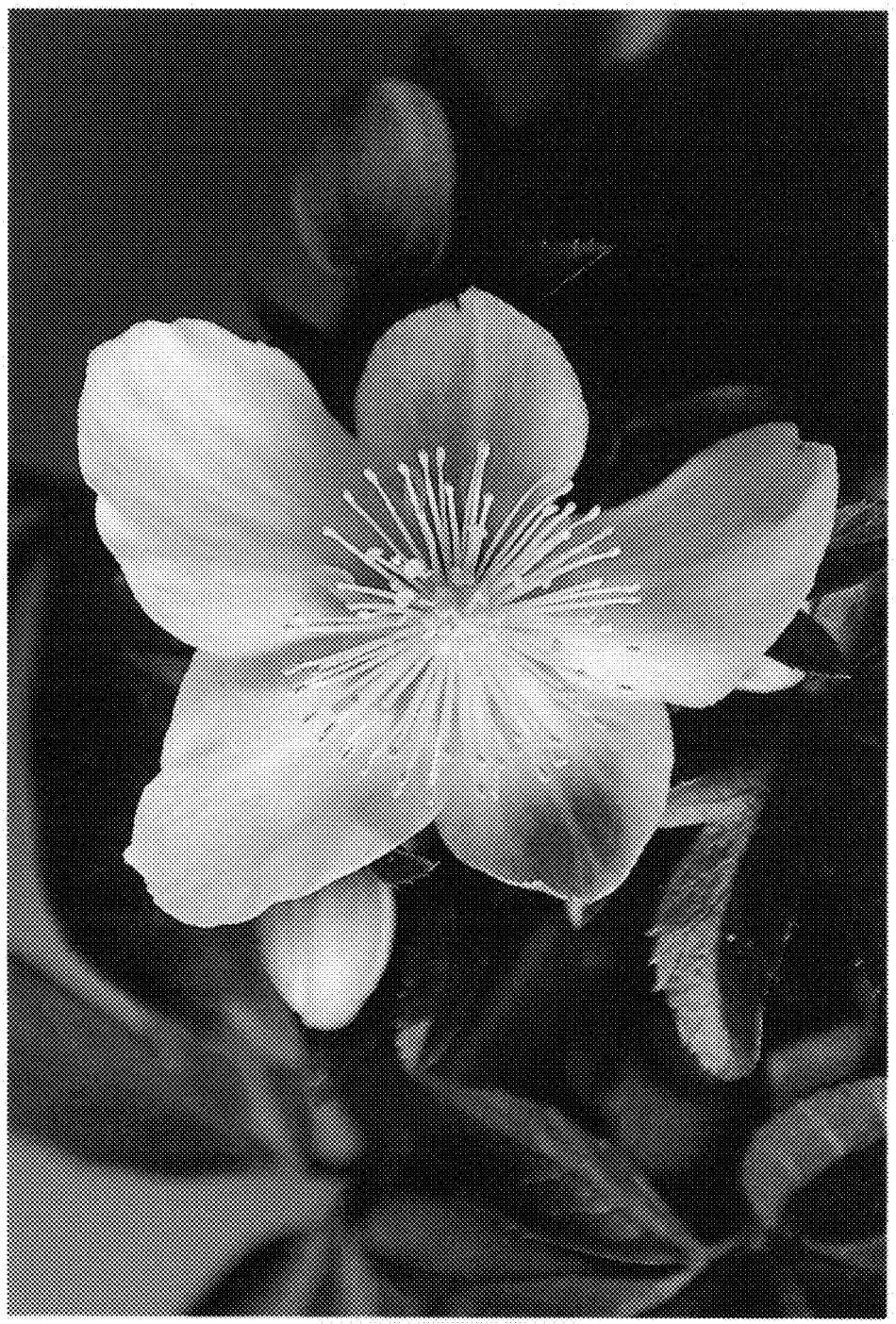

* * * * *